United States Patent
Doubler et al.

(10) Patent No.: US 8,663,290 B2
(45) Date of Patent: Mar. 4, 2014

(54) TOP LOADING POLYAXIAL BALL AND SOCKET FASTENER WITH SADDLE

(75) Inventors: Robert L. Doubler, Monroe, MI (US); John E. Hammill, Sr., Maumee, OH (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 116 days.

(21) Appl. No.: 13/397,182

(22) Filed: Feb. 15, 2012

(65) Prior Publication Data

US 2013/0110180 A1    May 2, 2013

Related U.S. Application Data

(60) Provisional application No. 61/552,515, filed on Oct. 28, 2011.

(51) Int. Cl.
  *A61B 17/70* (2006.01)
  *A61B 17/86* (2006.01)

(52) U.S. Cl.
  USPC .......................... 606/269; 606/270; 606/305

(58) Field of Classification Search
  USPC ............. 606/264–275, 300–321; 403/DIG. 7
  See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,483,334 A | 11/1984 | Murray |
| 4,693,240 A | 9/1987 | Evans |
| 4,708,510 A | 11/1987 | McConnell et al. |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,129,900 A | 7/1992 | Asher et al. |
| 5,133,717 A | 7/1992 | Chopin |
| 5,176,413 A * | 1/1993 | Westman .................. 285/321 |
| 5,501,684 A | 3/1996 | Schlapfer et al. |
| 5,549,608 A | 8/1996 | Errico et al. |
| 5,569,247 A | 10/1996 | Morrison |
| 5,591,166 A | 1/1997 | Bernhardt et al. |
| 5,716,357 A | 2/1998 | Rogozinski |
| 5,800,435 A | 9/1998 | Errico et al. |
| 6,485,491 B1 | 11/2002 | Farris et al. |
| 6,565,567 B1 | 5/2003 | Haider |
| 6,672,788 B2 | 1/2004 | Hathaway |
| 6,716,214 B1 | 4/2004 | Jackson |
| 7,066,937 B2 | 6/2006 | Shluzas |

(Continued)

FOREIGN PATENT DOCUMENTS

| | | |
|---|---|---|
| EP | 2301458 | 3/2011 |
| WO | WO0122893 | 4/2001 |

*Primary Examiner* — Matthew Lawson
(74) *Attorney, Agent, or Firm* — McHale & Slavin, P.A.

(57) ABSTRACT

The fastening system consists of the polyaxial ball and socket joint used in conjunction with a bone screw having threads on one end for use in anchoring to the spine and a spherical connector on the other end operating as a pivot point about which a connecting assembly moves in a polyaxial fashion. A substantially U-shaped connecting assembly has a lower receptacle that operates as a socket for housing a retainer ring within a retaining ring groove. The retaining ring cooperates with the connector assembly and a saddle that is positioned atop the spherical connector.

12 Claims, 5 Drawing Sheets

(56) References Cited

U.S. PATENT DOCUMENTS

| | | |
|---|---|---|
| 7,445,627 B2 | 11/2008 | Hawkes et al. |
| 2003/0118395 A1 | 6/2003 | Abels et al. |
| 2003/0153911 A1 | 8/2003 | Shluzas |
| 2005/0283157 A1* | 12/2005 | Coates et al. .......... 606/73 |
| 2006/0149240 A1 | 7/2006 | Jackson |
| 2006/0155277 A1 | 7/2006 | Metz-Stavenhagen |
| 2006/0235392 A1 | 10/2006 | Hammer et al. |
| 2006/0241599 A1 | 10/2006 | Konieczynski et al. |
| 2006/0241603 A1* | 10/2006 | Jackson ................ 606/61 |
| 2008/0177321 A1 | 7/2008 | Drewry et al. |
| 2008/0177322 A1 | 7/2008 | Davis et al. |
| 2008/0269809 A1 | 10/2008 | Garamszegi |
| 2011/0077694 A1* | 3/2011 | Biedermann et al. ......... 606/305 |
| 2011/0178559 A1 | 7/2011 | Barry |
| 2012/0116462 A1* | 5/2012 | Arambula ............... 606/305 |

* cited by examiner

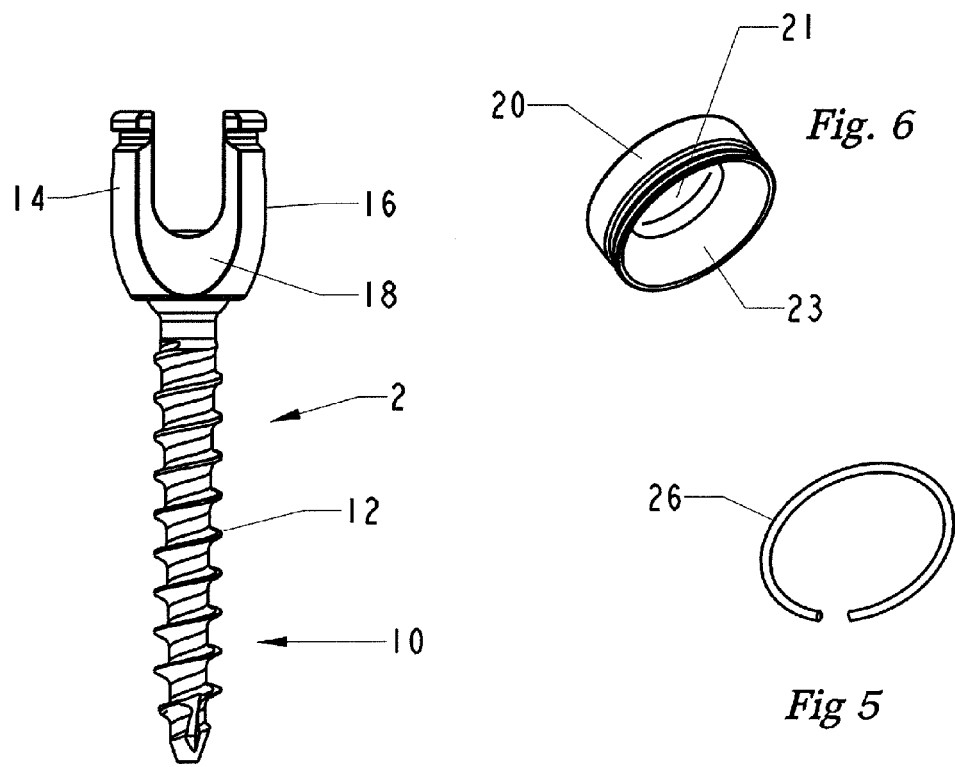
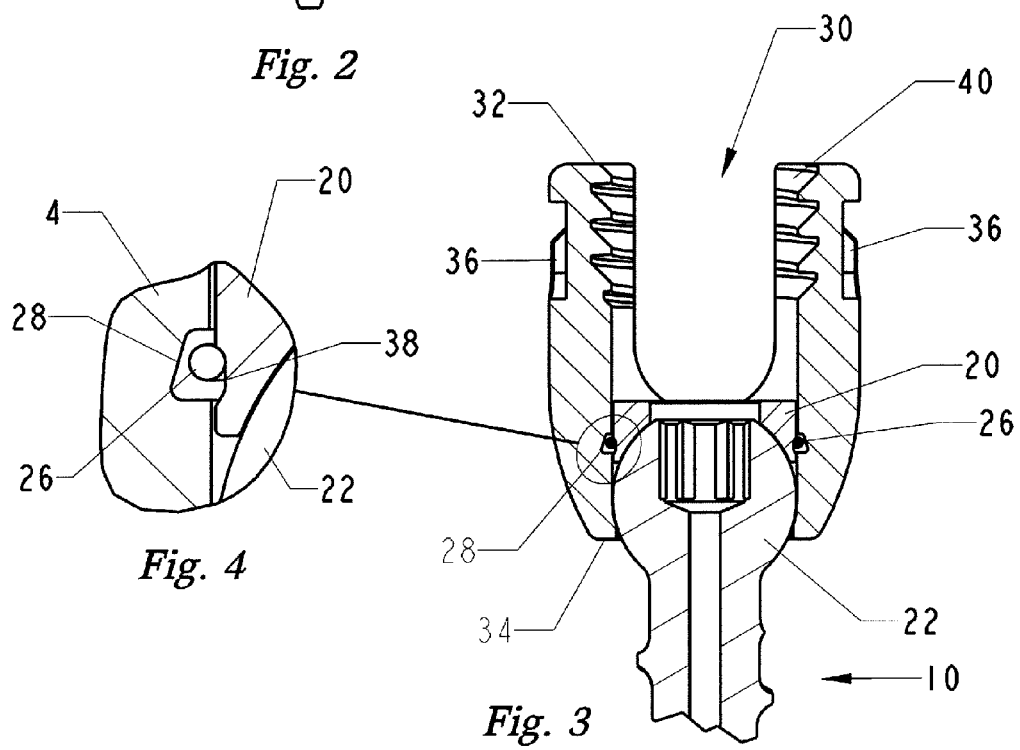

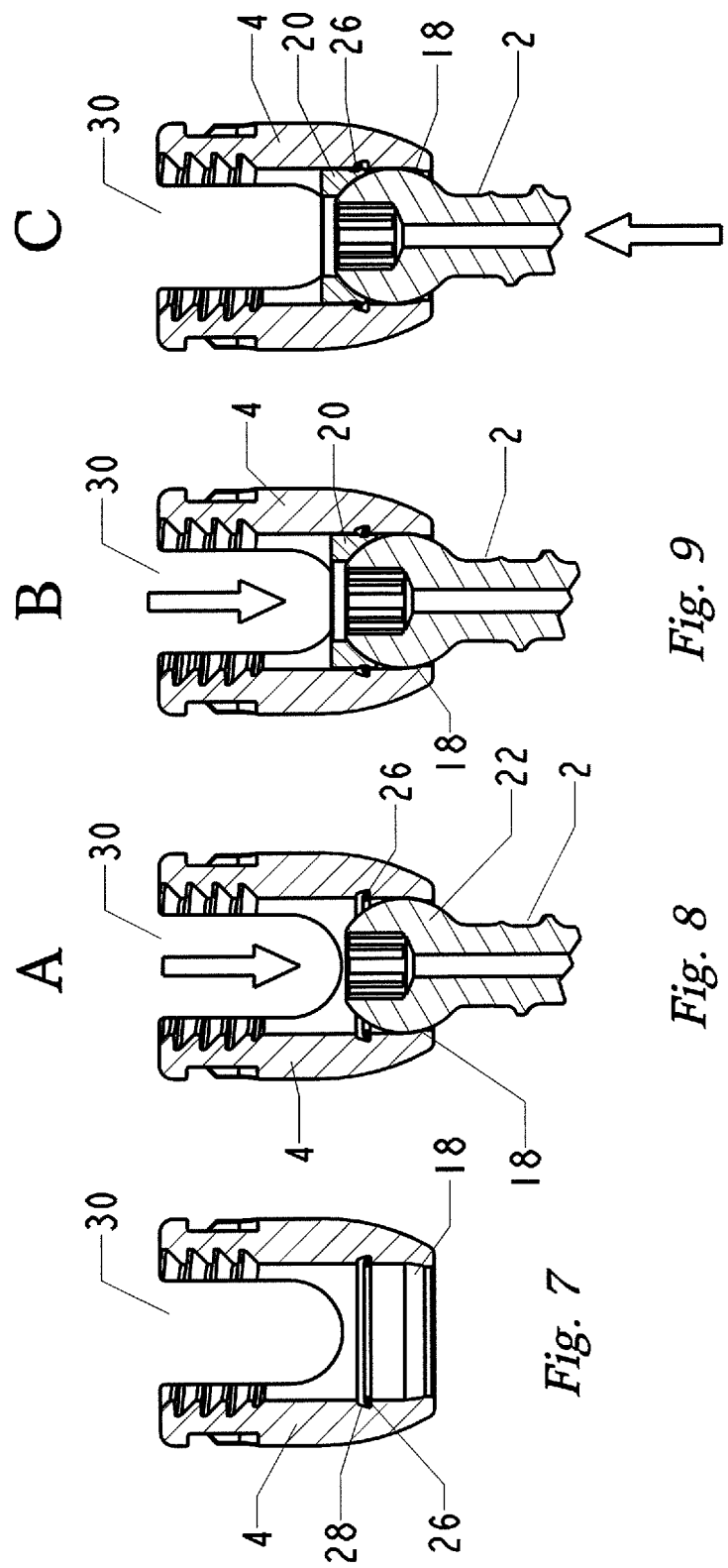

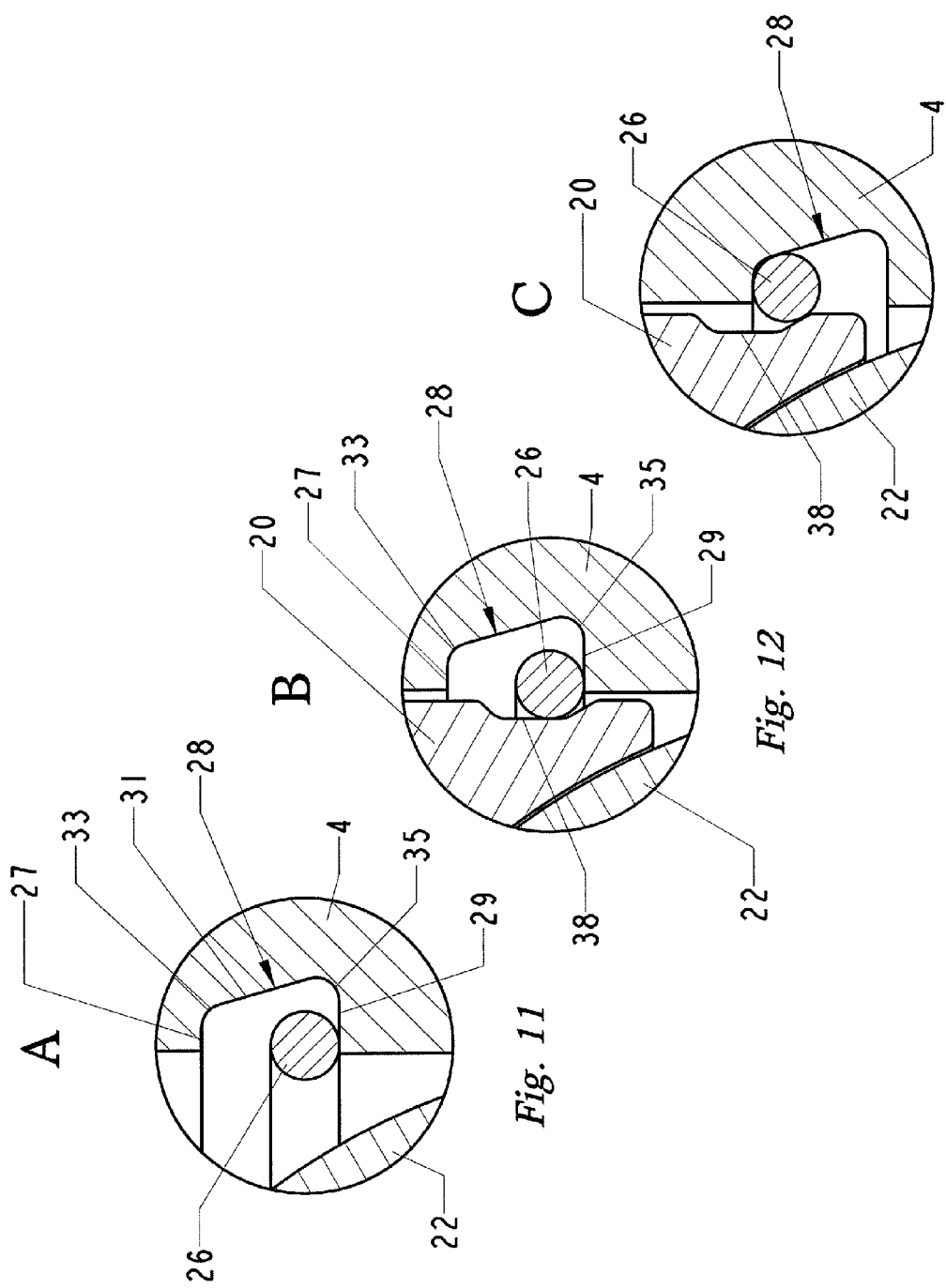

TOP LOADING POLYAXIAL BALL AND SOCKET FASTENER WITH SADDLE

RELATED APPLICATIONS

This application claims the benefit of provisional application No. 61/552,515, entitled Top Loading Polyaxial Ball and Socket Retainer, filed on Oct. 28, 2011, the entire contents of which is hereby expressly incorporated by reference. This application is related to U.S. patent application Ser. No. 13/397,141, filed on Feb. 15, 2012.

FIELD OF THE INVENTION

This invention is directed to the field of ball and socket fasteners, and in particular to a polyaxial ball and socket fastener adapted for use as a spinal implant.

BACKGROUND OF THE INVENTION

There are numerous ball and socket fasteners, however, when the application is applied to a particular product, the ball and socket must meet minimum specifications in order to be effective. For instance, in the field of spinal pathologies, the development of spinal fixation devices represents a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. Anchoring screws are inserted into the patient's spinal bones, and a series of connectors are used to rigidly link the rods and anchors.

A variety of designs exist, with each design addressing various aspects of the difficulties that arise when one re-shapes an individual's spine to follow a preferred curvature. Known spinal implant systems often correct one set of problems only to create new ones.

Common to all spinal implant systems is the necessity for proper anchoring to the bone so as to provide support for the aforementioned components. While bone screws are commonly used for anchoring, the use of a polyaxial design has proven very effective in allowing a surgeon the flexibility to secure an installation with minimal strain on the individual.

For this and other reasons, screws located in bone structure typically use a polyaxial base and a specially designed connector member for attachment to a component such as an alignment rod. A problem with the current technology is that bone structure cannot be determined until the patient's bone is exposed. This problem requires a large inventory of various sized implants to be on hand during every surgery. The surgeon must search through the inventory to assembly a combination based on his prediction of what will be required. Even if an implant combination is predicted, the anchoring screw may still require angular insertion due to muscle structure or nerve locations. Any movement of muscle and other tissue increases the difficulty of the operation and can be a major trauma to the patient. Still yet, bone condition may require oversize threads to achieve a suitable purchase to the bone. As a consequence, the surgeon must either maintain a large inventory of anchoring devices, or have a vendor standing by with a large inventory of anchoring devices that will hopefully meet the individual requirements.

One of the problems with a polyaxial pedicle screw is the lack of a stabilized angular placement position during installation. Once a polyaxial pedicle screw is inserted into the bone, the connector component portion has yet to receive a connecting rod leaving the connector assembly to flop over making it difficult for the Surgeon to grasp while in the midst of surgery. This problem is compounded by the need to align multiple component heads for receipt of a connecting rod.

DESCRIPTION OF THE PRIOR ART

U.S. Pat. No. 7,066,937 discloses an apparatus including a housing having a first passage configured to receive a longitudinal member and a second passage with an axis transverse to the first passage; a fastener extending through an opening in the housing and being moveable relative to the housing; the second passage of the housing having an indentation, the indentation including an axially extending surface at least partially defining the second passage and an upper surface extending transverse to the axially extending surface, a spacer received in the second passage of the housing, the spacer having a radial surface below the upper surface of the indentation; and a member contacting the upper surface of the indentation and the radial surface of the spacer that applies an axial force to the spacer to prevent relative movement between the fastener and the housing and holding the fastener in any one of a plurality of angular positions relative to the housing.

U.S. Pat. No. 6,485,491 discloses a multi-axial bone anchor assembly that includes a saddle member, a bone anchoring member and a washer. The saddle has a channel that receives a rod. A snap ring secures the washer in the saddle member. The snap ring engages a snap ring recess. The disclosed structure would not prevent relative movement between a fastener and a housing and would not hold a longitudinal axis of the fastener in any one of a plurality of desired angular positions relative to a longitudinal of a passage in the housing when a rod, longitudinal member, is disengaged from a spacer. The patent does not teach an arrangement where a spacer necessarily engages a fastener when a rod, longitudinal member, is so disengaged.

A conventional polyaxial bone screw typically consists of a single shaft with a coarse thread at one end for threading into the bone. A spherical ball is positioned at an opposite end for coupling to a connecting member. For example, a number of patents exist for bone screw anchoring assemblies that include a U-shaped connector element which acts as a saddle for attachment to an alignment rod. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion designed for threadingly engaging a semi-spherical cup for use with a specially designed alignment rod. The alignment rod includes spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are designed with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employs connectors that join the support rods and anchoring screws. The connectors eliminate unwanted relative motion between the rod and the screws, thereby maintaining the patient's spine in a corrected orientation.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths.

U.S. Pat. No. 7,445,627 discloses a fastener and a bone fixation assembly for internal fixation of vertebral bodies. According to one exemplary embodiment, a tulip assembly is employed, the tulip assembly includes a non-circular surface disposed on its outer surface. A fastener is coupled to the tulip assembly and positionable to retain the tulip assembly on the head of a screw. A cap having an outer surface and a plurality of inner protrusions mateably connects to the non-circular surface on the tulip body to compress the tulip assembly to secure a rod.

U.S. Publication No. 2008/0177322 discloses a spinal stabilization system that includes bone fastener assemblies that are coupled to vertebrae. Each bone fastener assembly includes a bone fastener and a collar. The bone fastener has a head portion having at least a first cross-sectional shape in a first plane, and a second cross-sectional shape in a second plane. The collar has a circular opening in the bottom, with a relief extending from the circular opening. The second cross-sectional shape of the bone fastener is keyed to the opening to permit insertion of the bone fastener into the collar assembly from the bottom. After insertion, the bone fastener is rotated to prohibit removal of the bone fastener from the collar. The collar can then be rotated and/or angulated relative to the bone fastener. An elongated member can be positioned in the collar and a closure member is then used to secure the elongated member to the collar.

U.S. Publication No. 2006/0241599 discloses a polyaxial fixation device having a shank with a spherical head formed on a proximal end thereof, and a receiver member having an axial passage formed therein that is adapted to polyaxially seat the spherical head of the shank. The polyaxial bone screw further includes an engagement member that is adapted to provide sufficient friction between the spherical head and the receiver member to enable the shank to be maintained in a desired angular orientation before locking the spherical head within the receiver member.

U.S. Publication No. 2006/0235392 discloses a system for connecting a fastener element (e.g., a pedicle screw) relative to a rod for the purposes of vertebral fixation. The system may permit multi-axial movement between the fastener element and the rod. Further, the system may permit the angular relationship between the fastener element and the rod to be held in a desired orientation.

U.S. Publication No. 2006/0155277 discloses an anchoring element for securing a rod on a vertebra, that comprises a retaining means for receiving the rod, a safety element placed on the retaining means, a securing element which can be placed on the body of the vertebra, and a clamping device which is arranged between the retaining means and the securing element. The clamping device includes a ring-shaped mount, a partially conical-segment shaped bearing and an intermediate element which is embedded in the mount and which engages the bearing, whereby the mounting is moveable in a removed state in relation to the bearing, whereas the mount is maintained in a clamped state on the bearing by means of the intermediate element. The mount is rigidly connected to the retaining means and the bearing is rigidly connected to the securing element.

U.S. Publication No. 2006/0149240 discloses a polyaxial bone screw assembly that includes a threaded shank body having an upper capture structure, a head and a multi-piece retainer, articulation structure. The geometry of the retainer structure pieces correspond and cooperate with the external geometry of the capture structure to frictionally envelope the retainer structure between the capture structure and an internal surface defining a cavity of the head. The head has a U-shaped cradle defining a channel for receiving a spinal fixation or stabilization longitudinal connecting member. The head channel communicates with the cavity and further with a restrictive opening that receives retainer pieces and the capture structure into the head but prevents passage of frictionally engaged retainer and capture structures out of the head. The retainer structure includes a substantially spherical surface that mates with the internal surface of the head, providing a ball joint, enabling the head to be disposed at an angle relative to the shank body.

U.S. Pat. No. 6,716,214 discloses a polyaxial bone screw having a bone implantable shank, a head and a retaining ring. The retaining ring includes an outer partial hemispherical surface and an inner bore with radially extending channels and partial capture recesses. The shank includes a bone implantable body with an external helical wound thread and an upwardly extending capture structure. The capture structure includes at least one spline which extends radially outward and has a wedged surface that faces radially outward therefrom. The capture structure operably passes through a central bore of the retaining ring while the spline passes through a suitably shaped channel so that the spline becomes positioned above the head, at which time the shank is rotated appropriately and the shank is drawn back downwardly so that the spline engages and seats in the capture recess. The head includes an internal cavity having a spherical shaped surface that mates with the ring surface and has a lower restrictive neck that prevents passage of the ring once the ring is seated in the cavity.

U.S. Pat. No. 6,565,567 discloses a pedicle screw assembly for use with a rod for the immobilization of bone segments. The assembly is comprised of a screw, a polyaxial housing for receiving the screw, a washer, a set screw, and a cup-shaped cap. The lower portion of the housing terminates in a reduced cross-sectional area, which engages the bottom of the screw head. When the screw is placed inside the polyaxial housing and the screw is secured into the bone, the polyaxial housing is pivotable with three degrees of freedom. The housing includes a top portion with a pair of upstanding internally threaded posts. A washer is inserted between the head of the screw and the rod. A cap, having a bottom, with a pair of posts accommodating openings and a lateral cross connector, is placed over the posts so that the cross connector engages the rod. The cross connector and washer have concave generally semi-cylindrical rod engaging surfaces to prevent the rod from rotating or sliding within the housing once the set screw is tightened. A set screw is threaded into the housing posts to secure the rod within the housing. The washer has a roughened lower surface which, in conjunction with the reduced cross-sectional area at the bottom of the housing, securely clamps and locks the housing to the screw head when the set screw is tightened.

U.S. Pat. No. 5,501,684 discloses an osteosynthetic fixation device which consists of a fixation element which has a conical head section and an anchoring element abutting it which is for attachment into the bone. The fixation device also consists of a spherically formed, layered, slotted clamping piece which has a conical borehole for installation of the conical head section, and which is meant for locking within a connecting piece equipped with a spherically shaped layered borehole. Fixation piece has an axially arrayed tension element, permitting axial displacement and wedging of conical head section in the borehole that corresponds with it. The fixation device is appropriate for use as a plate/screw system, an internal or external fixator, and in particular for spinal column fixation.

U.S. Pat. No. 4,693,240 discloses a bone pin clamp for external fracture fixation. The apparatus comprises rotation, slide and housing elements nested one within the next, each such element having an aperture to receive a pin there through, and the rotation and slide elements respectively affording pin adjustment in azimuth and zenith, and in height, relative to the housing element. A locking mechanism including a common actuator member is operable simultaneously to lock the pin and rotation and slide elements in the housing element. In a preferred form, the housing element serves as a cylinder with the slide element as a keyed piston therein, and the rotation element is a disc located between a screw and annular thrust members engaged in the piston, the piston and disc being split respectively to lock by expansion and compaction under screw action towards the thrust members.

U.S. Pat. No. 4,483,334 discloses an external fixation device for holding bone segments in known relation to each other. The device includes a pair of bone clamp assemblies each secured to bone pins extending from the bone segments, a bridge extending between the pin clamp assemblies, and a specialized high friction universal assembly connecting the bridge to each of the pin clamp assemblies.

U.S. Pat. No. 4,273,116 discloses an external fixation device for reducing fractures and realigning bones that includes sliding universal articulated couplings for enabling easy adjustment and subsequent locking of connections between Steinmann pins and tubular tie-rods. The couplings each include a split, spherical adapter sleeve which is embraced by the matching inner surface of an open ring portion of a coupling locking clamp having clamp lugs tightenable against a block by means of a nut-and-bolt assembly. Further nut-and-bolt assemblies are disposed in elongated slots in the blocks and cooperate with associated clamping members to clamp the Steinmann pins to the blocks after adjustment in two orthogonal directions and optional resilient bending of the pins.

U.S. Pat. No. 6,672,788 discloses a ball and socket joint incorporating a detent mechanism that provides positive biasing toward a desired position. The ball and socket joint can be used in flexible supports that hold and support items such as lamps, tools and faucets. The detent mechanism comprises two corresponding parts, one in the ball portion and the second in the socket portion of the joint. The first detent part is a protrusion of some type and the second detent part is a groove or indentation that is adapted to accept and engage the protrusion. If the ball contains the detent protrusion, then the socket contains the detent indentation. And conversely, if the socket contains the detent protrusion, then the ball contains the detent indentation. The detent tensioning force can be provided by a spring or a spring band, the characteristics of the material from which the joint is made, or by some other similar tensioning device.

U.S. Publication No. 2003/0118395 discloses a ball and socket joint, which has a housing, a ball pivot mounted pivotably in the housing, and a sealing bellows, which is fastened to the housing and is mounted on the ball pivot slidably via a sealing ring provided with two legs. A first leg of the two legs is in contact with the ball pivot under tension and the second leg meshes with the wall of the sealing bellows. The second leg is, furthermore, fastened in an anchoring ring arranged at least partially in the wall of the sealing bellows.

U.S. Pat. No. 4,708,510 discloses a ball joint coupling assembly that permits universal movement and positioning of an object with respect to a vertical support shaft. Quick release/lock action is provided by a ball joint assembly having a housing in which a ball and piston are movably coupled. The ball is captured between annular jaw portions of the housing and piston, with locking action being provided by gripping engagement of the piston jaw portion and the housing jaw portion. The ball member is gripped in line-contact, compressive engagement by the annular edges of the piston jaw and housing jaw on opposite sides of the ball. The piston is constrained for axial movement within the housing with locking engagement and release being effected by rotation of a threaded actuator shaft.

U.S. Pat. No. 3,433,510 discloses a swivel structure for rigidly joining first and second parts together. A first member is connected to the first part and a second member is connected to the second part. An intermediate hollow member interconnects the first and second members together. An enlarged outer end portion is provided on the first member and includes a plurality of locking means thereon. Means are provided on the second member for engaging one of the locking means. Means are provided for threadably joining the hollow member and the second member together. A slot is provided in the hollow member and includes an enlarged entrance which passes the enlarged outer end portion and which also includes a restricted opening opposite the threaded joining of the hollow member and the second member together. The portion surrounding the restricted opening opposes the forces imparted against the outer end portion as the second member is threadably joined to the hollow portion and bears against the outer end portion.

U.S. Patent Publication No. 2008/0269809 discloses a bottom loading pedicle screw assembly. The device includes a pedicle screw and a connector member. The pedicle screw includes a threaded lower portion while the upper portion includes a groove sized to accept a clip member. The clip member includes a spherical outer surface. In operation the clip is placed within the groove and the assembly is pressed through the opening in the bottom of the connector member. While the device is bottom loading, the device will separate when the pedicle screw is aligned with the connector member. The construction of the clip member allows the clip to collapse sufficiently to pass back through the opening when the screw is positioned in alignment with the connector, requiring the connection to bone be placed at an angle with respect to the connector for proper operation.

Thus, what is needed is a polyaxial ball and socket joint that can be adapted for use in a spinal fixation system that includes the advantages of known devices, while addressing the shortcomings that they exhibit. The system should allow component interchangeability at point of installation, thereby addressing a wide variety of spinal deformities with less components. In addition, the system should allow the stabilized angular placement position of the connector components during installation.

SUMMARY OF THE INVENTION

Briefly, the present invention is a polyaxial ball and socket joint capable of snap together assembly. Disclosed is an exemplary embodiment of the ball and socket fastening system adapted for use in a spinal fixation system for reshaping the spine of a patient. The fixation system includes the polyaxial ball having a bone screw extending outwardly therefrom for use in anchoring to the spine and a connector member that includes a socket constructed and arranged to accept a saddle and the polyaxial ball. In the disclosed embodiment, the connector member assembly is illustrated as a U-shaped connector member having a receptacle for housing a split ring retainer within a ring groove.

The socket is receptive to the spherical connector which is inserted through an aperture in the top of the connector assembly. The spherical polyaxial ball when fully inserted into the connector assembly is seated on a spherical base at the bottom of an internal passageway within the connector assembly. A split retaining ring is located within a groove formed in a wall of the internal passageway. A saddle having a spherical surface formed on a lower end is then inserted into the internal passageway. The outer cylindrical surface of the saddle includes a groove that extends completely around the outer cylindrical surface of the saddle. As the saddle moves past the retainer ring the ring will expand within the groove formed within the internal passageway on the connector assembly until the groove formed on the saddle comes into alignment with the split ring. When the grooves on the connector assembly and saddle are in alignment, the split ring will contract thereby mechanically connecting the saddle to the connector assembly.

A set screw or nut can then be utilized to press a connecting rod into contact with the saddle which in turn will contact the spherical surface of the ball while simultaneously causing the lower portion of the ball to wedge the ball against the inner surface of the connector member immobilizing the connection.

During surgery a surgeon can determine the most advantageous bone screw or other type of bone connection to match the connecting assembly. The bone connector is then coupled to the connector assembly by inserting or snapping the spherical connector and then the saddle into the socket of the connecting assembly. In operation, the spherical connector is pushed past the retainer ring whereby the ring expands past the largest diameter of the connector. The saddle is then pushed past the retainer ring whereby the ring expands past the largest diameter of the saddle until the groove on the saddle aligns with the split ring and allows the split ring to contract. This mechanical connection serves to prohibit removal of the connector while still allowing polyaxial movement between the spherical ball and the connector member. The saddle is resiliently biased against an upper surface of the spherical connector and engages the spherical connector so as to keep the U-shaped connector member in position during installation. A surgeon can easily move the spherical connector member into a preferred position and the resilient split ring will keep sufficient force between the upper surface of the spherical connector and the first groove so as to maintain the spherical connector in a selected position relative to the connector assembly. This facilitates the installation of the rod as the U-shaped connector not only can be rotated into a position for proper placement of the connecting rod but the proper angle of the saddle can also be maintained while allowing the surgeon to align additional screws for ease of rod placement.

Because of the flexibility and resilience of the split retention ring, the mating parts do not require fine tolerances and are economical to manufacture. The system is modular, employing a collection of anchoring assemblies that are linked, via various connectors, to strategically-arranged stabilizing rods.

The connector assemblies are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a polyaxial ball and socket fastener for use in a spinal stabilization system.

Another objective of the invention is to disclose the use of a polyaxial ball and socket system that is capable of securing various anchors to various connector assemblies so as to reduce the amount of inventory required to meet a particular installation.

It is another objective of the present invention to provide a polyaxial bone screw assembly for a spinal fixation system that permits component adjustment during installation, thereby enabling satisfactory correction of a wide variety of spinal deformities.

It is an additional objective of the present invention to provide a bone screw assembly that includes a split ring locking mechanism that is simple, strong and reliable.

It is yet another objective of the present invention to provide a spinal fixation system that requires minimum tools for installing of an anchor and securing element.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 2 is a side view of the ball and socket fastener;

FIG. 3 is a cross sectional view of the ball and socket fastener assembled;

FIG. 4 is an enlarged view of the circled area in FIG. 3;

FIG. 5 is a perspective view of a split ring;

FIG. 6 is a perspective view of the saddle;

FIG. 7 is a cross sectional side view of the connector assembly with the split ring mounted within a groove formed in the internal passageway;

FIG. 8 is a cross sectional side view of the spherical ball connector of the bone anchor within the connector assembly having just moved past the split ring;

FIG. 9 is a cross sectional side view of the bone anchor, connector assembly, and saddle with the split ring connecting the saddle to the connector assembly;

FIG. 10 is a cross sectional side view of the bone anchor, connector assembly, saddle and split ring illustrating how the split ring will restrict the saddle from coming backout;

FIG. 11 is an enlarged sectional view of the split ring illustrating how the split ring allows the spherical head of the bone anchor to pass;

FIG. 12 is an enlarged sectional view of the split ring illustrating how the split ring operatively engages the connector assembly and the saddle;

FIG. 13 is an enlarged sectional view illustrating how the split ring restricts the saddle from backing out of the connector assembly;

DETAILED DESCRIPTION OF THE INVENTION

Figure 1:
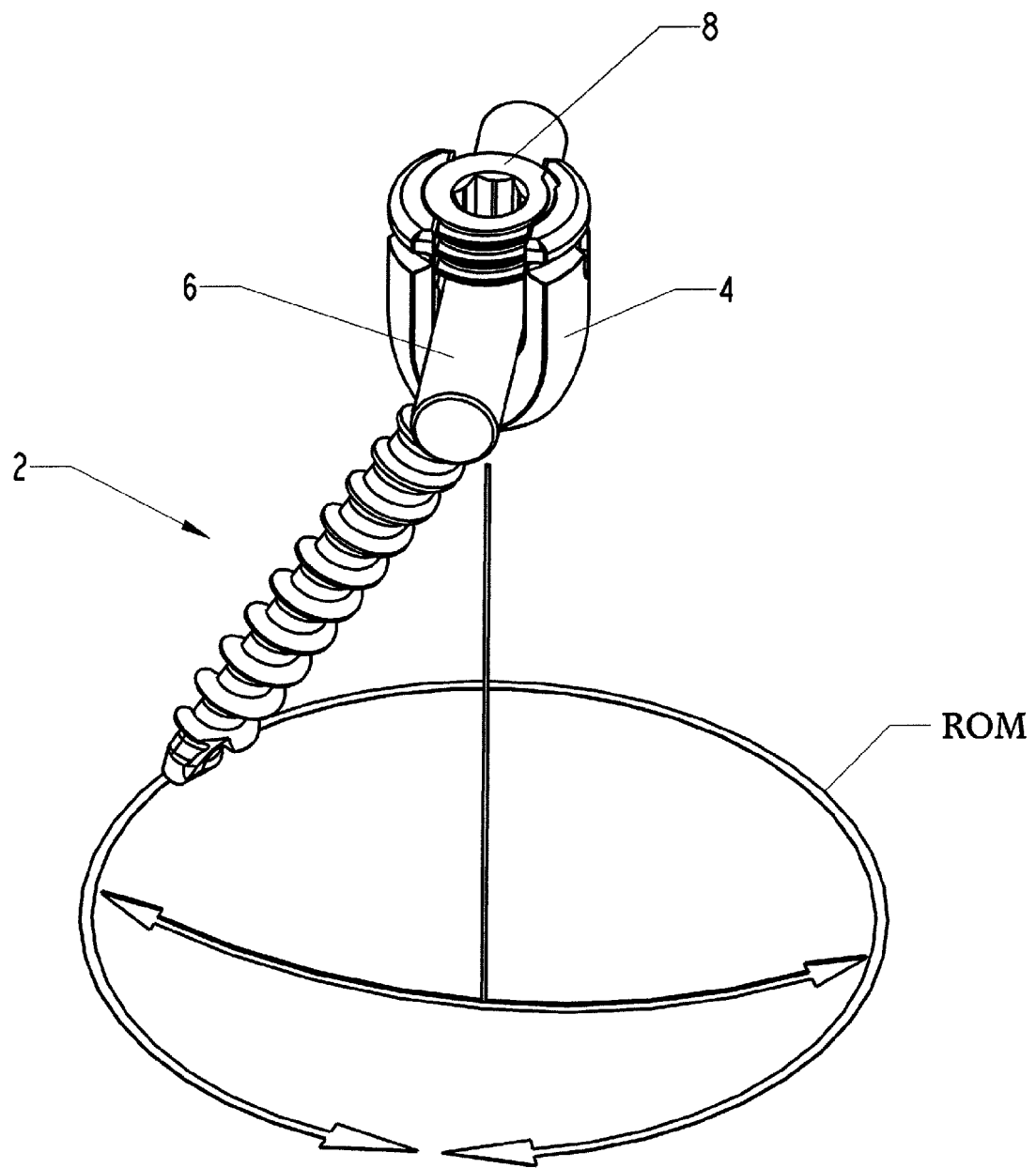
FIG. 1 is a top perspective view of the ball and socket fastener with the anchoring member illustrating the polyaxial cooperation between the spherical ball and the connector assembly.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

FIG. 1 is a top perspective view of the ball and socket fastener with the anchoring member illustrating the polyaxial cooperation between the spherical ball of the bone anchor (2) and the connector assembly (4). The polyaxial ball and socket fastening system is adapted for use in a spinal fixation system. The fastening system includes a spherical ball connector secured or formed integrally with a bone anchor (2) and connecting assembly (4) that includes a snap-in type receptacle for the spherical ball connector to form a polyaxial joint allowing a range of motion (ROM). The connector assembly (4) also includes a receiver that may be used in conjunction with a connecting rod member (6) for securing at least two bone anchors (2) together. A set screw (8) will fasten a connecting rod (6) to the connector assembly (4).

As shown in FIG. 2, the bone anchor (2) of the preferred embodiment is a bone screw including a threaded shank (10) having a length with at least one helical thread (12) formed along the length thereof. It is important to note that the proportions of the bone anchor (2) depicted are for illustrative purposes only and variations in the length of the shank, diameter of the screw, thread pitch, thread length, number of thread leads, shank induced compression and the like may be varied without departing from the scope of the invention. The upper end of the connector assembly (4) is generally U shaped having a first upstanding side wall (14) and a second opposite upstanding side wall (16).

As shown in FIG. 3, the upper end of the threaded shank (10) is a spherical ball connector (22) having a predetermined diameter. A driver receptacle (24), configured as a recess, is located along the upper surface of the spherical ball connector (22) for use in installing the bone anchor (2) by use of driving tool having an engaging projection that is complimentary to the shape of the driver receptacle (24). It should be noted that the driver receptacle (24) may be any shape, male or female, suitable for cooperation with a driving tool to rotate the bone anchor (2) into its final position.

The U-shaped connector assembly (4) is illustrated having a split retaining ring (26) that is insertable into a split ring groove (28). The U-shaped connector assembly (4) includes an internal passageway (30) that extends from a first end (32) to a second end (34). The diameter of the internal passageway (30) being greater than the diameter of the spherical ball connector (22) at said first end (32) and the diameter of the internal passageway (30) at said second end (34) being smaller than the diameter of the spherical ball connector (22). The U-shaped connector assembly (4) includes a base with a pair of U-shaped openings forming a first upstanding side wall (14) and second opposite upstanding side wall (16). The side walls preferably include a recessed flute (36) constructed and arranged to provide a gripping surface that cooperates with a tool (not shown) to allow a physician to apply a torque to the connector assembly (4) during tightening or removal of a set screw (8), or for use in attachment to an extender tube (not shown). Extender tubes are well known in the art of minimally invasive spinal procedures. The upper end of the internal passageway (30) of connector assembly (4) beginning at the first end (32) includes a threaded portion (40) that is configured to threadably engage set screw (8).

FIG. 4 is an enlarged view of the circled area in FIG. 3. In the assembled position, as shown, split retaining ring (26) is located partly within the split ring groove (28) in the connector assembly (4) and within a second groove (38) formed about the circumference of saddle (20). In this orientation the split retaining ring (26) acts to resist withdrawal of the bone anchor (2) from the connector assembly (4).

FIG. 5 is a perspective view of a split ring (26). FIG. 6 is a perspective view of the saddle (20). The saddle (20) includes an aperture (21) that permits a tool to pass through the saddle (20) and engage the driver receptacle (24) within the spherical ball connector (22). The upper surface of the saddle (20) is generally flat and the lower surface (23) is spherical and is configured to conform to the surface of the spherical ball connector (22).

FIGS. 7 through 10 illustrate the assembly of the locking polyaxial ball and socket fastener. FIG. 7 is a cross sectional view of connector assembly (4) with the split retaining ring (26) positioned in split ring groove (28). FIG. 8 shows the bone anchor (2) after insertion from the top of the connector assembly (4). The spherical ball connector (22) having been inserted past the split retaining ring (26) and being seated on an inner spherical surface (18) located in the internal passageway (30) adjacent the second end of the connector assembly (4). FIG. 9 shows the combination of the bone anchor (2) with connector assembly (4) and the saddle (20) being operatively connected by the split retaining ring (26). FIG. 10 illustrates how the split retaining ring (26) resists withdrawal of the bone anchor (2) from the connector assembly (4).

FIG. 11 illustrates the position of the split retaining ring (26) within the groove (28) after the spherical ball connector (22) has been inserted past the split retaining ring (26), as shown in FIG. 8. FIG. 12 illustrates the position of the split retaining ring (26) within the first groove (28) on the connector assembly (4) and the second groove (38) on the saddle (20) after the saddle (20) has been inserted into the connector assembly (4) and in the operative position, as shown in FIG. 9. FIG. 13 illustrates the position of the split retaining ring (26) within split ring grooves (28) and (38) when the a force is acting on the bone anchor (2) to move it upwards relative to the connector assembly, as shown in FIG. 10. The split ring grove (28) formed in the connector assembly (4) includes an upper wall (27), a lower wall (29) and an inclined side wall (31). The lower wall (29) extends radially outward a greater distance that upper wall (27). The side wall (31) is angularly positioned wherein the junction of the lower end wall (29) and side wall (31) forms a first annulus (35) having a first diameter (D1) and the junction of the upper end wall (27) and side wall (31) forms a second annulus (33) with a second diameter (D2). The second split ring groove (38) includes a straight surface bounded on the upper and lower edge thereof by inclined surfaces.

Figure 14:
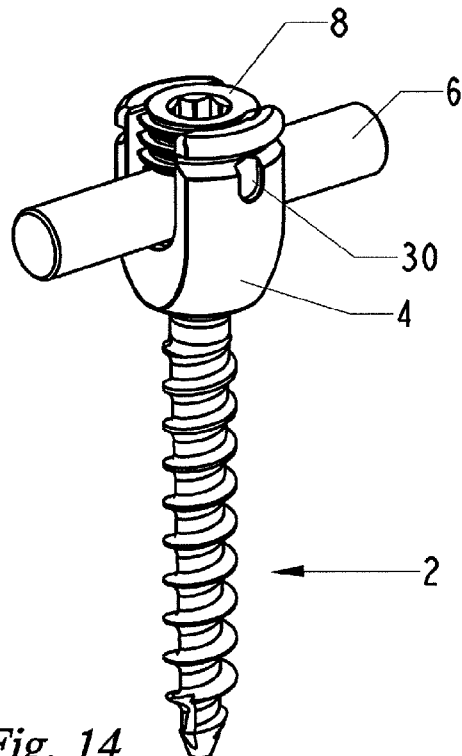
FIG. 14 is a perspective view of the assembled bone anchor, connector assembly, rod and set screw.

FIG. 14 is a perspective view of the device in an assemble condition. As shown, bone anchor (2) is connected to connector assembly (4) and the rod (6) is connected to the connector assembly (4) view set screw (8).

Figure 15:
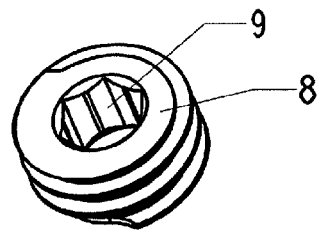
FIG. 15 is a perspective view of the set screw.
Figure 16:
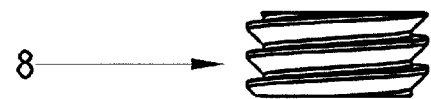
FIG. 16 is a side view of the set screw.

FIG. 15 is a perspective view of the set screw (8). Set screw (8) includes a socket (9) configured to receive a tool to rotate the set screw (8) into the threaded portion (40) of the connector assembly (4). FIG. 16 is a side view of the set screw (8) showing the external threads thereon.

Figure 17:
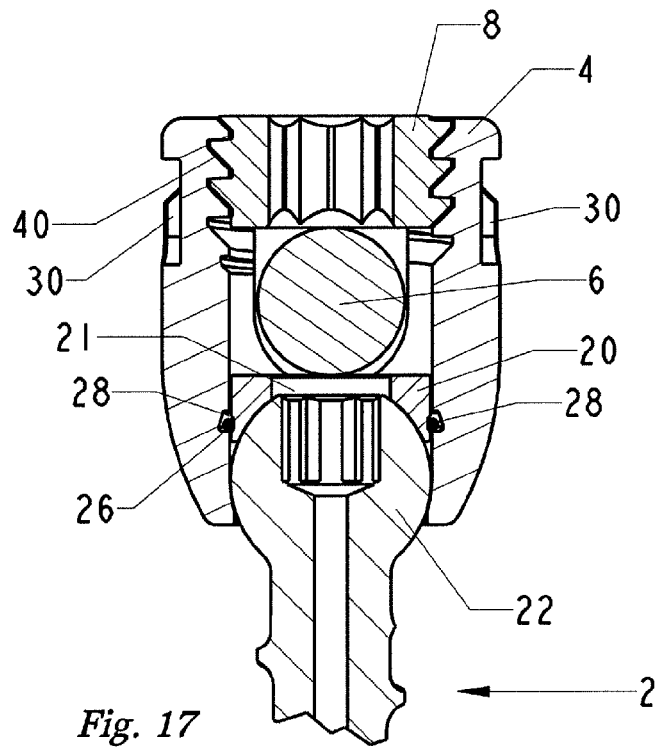
FIG. 17 is a sectional side view of the total assembly.

FIG. 17 is a sectional side view of the total assembly. As shown, the spherical ball connector (22) of the bone anchor (2) is positioned in the lower end of the connector assembly (4). The mechanical cooperation of split retaining ring (26) with split ring groove (28) on the connector assembly (4) and the second split ring groove (38) on the saddle (20) facilitates retention of the bone anchor (2) within the connector assembly (4). The rod (6) is positioned atop the flat top surface of saddle (20) and is secured into position by set screw (8). The set screw (8) imparts a downward force on rod (6) which in turn imparts a downwards force on saddle (20) which in turn exerts a downward force on the spherical ball connector (22) which in turn imparts a force on the lower inner surface (18) located within the internal passageway (30) adjacent the second end (34) thereby locking the polyaxial connection between the bone anchor (2) and the connector assembly (4).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An assembly for a polyaxial screw comprising:
    a bone anchor having a spherical connector and a shank with at least one thread formed along a length of said shank and,
    a connector assembly having a first side wall and a second side wall each having a U-shaped opening, said connector assembly including an internal passageway having a wall that extends from a first end to a second end, a diameter of the internal passageway being greater than the diameter of the spherical connector at said first end and the diameter of the internal passageway at said second end being smaller than the diameter of the spherical connector, said internal passageway further including a first groove formed in said wall of the internal passageway, and a retaining ring having a circular cross section is positioned within said first groove,
    said first groove includes an upper end wall, a lower end wall and a sidewall of said first groove therebetween, said sidewall of said first groove is angularly positioned wherein a junction of the upper end wall and said sidewall of said first groove forms a first annulus having a first diameter and a junction of the lower end wall and said sidewall of said first groove forms a second annulus having a second diameter, said second diameter greater than said first diameter; and
    a saddle being generally cylindrical in shape and having a generally flat upper surface and a lower surface that is generally spherical and is configured to conform to the surface of the spherical connector, and a second groove formed about the circumference of said generally cylindrical saddle,
    wherein as the shank is inserted into the first end of said internal passageway and out of the second end of the internal passageway the spherical connector is moved past the retaining ring which is initially expanded to allow the spherical connector to pass and once past the retaining ring will return to its unexpanded state, and said saddle is inserted into the first end of said internal passageway and as the saddle is moved toward said spherical connector the retaining ring is initially expanded and will return to its unexpanded state whereby said retaining ring simultaneously engages said first annulus formed from said junction of said upper end wall and said sidewall of said first groove and said second groove to prohibit the removal of the saddle from the connector assembly.

2. The assembly for a polyaxial screw as set forth in claim 1, wherein the retaining ring is a split ring and can expand in diameter within said first groove up to the second diameter of the second annulus as the spherical connector is moved past the split ring.

3. The assembly for a polyaxial screw as set forth in claim 2, wherein the split ring prohibits removal of the spherical connector when the split ring is positioned between said saddle and the first annulus formed within the said first groove.

4. The assembly for a polyaxial screw as set forth in claim 2, wherein the split ring is resiliently biased between said second groove formed in said saddle and said first annulus when the split ring is positioned between the saddle and the first annulus formed within the first groove whereby the connector assembly can be moved into an implanted position and the split ring will keep sufficient force on the spherical connector to maintain the spherical connector in a selected position relative to the connector assembly.

5. The assembly for a polyaxial screw as set forth in claim 1, wherein an upper surface of said spherical connector includes a driver receptacle wherein said bone anchor can be operatively engaged by a driving tool to rotate said bone anchor into its final position.

6. The assembly for a polyaxial screw as set forth in claim 5, wherein said saddle includes an aperture configured to allow a tool to pass through said saddle and engage said recess within the spherical ball connector.

7. The assembly for a polyaxial screw as set forth in claim 1, wherein the internal passageway at the second end of said connector assembly has a generally spherical surface and is constructed and arranged in configuration to be complimentary to the spherical surface on the spherical connector.

8. The assembly for a polyaxial screw as set forth in claim 1, further including a connecting rod sized and configured to be received within the U shaped opening of said first side wall and said second side wall.

9. The assembly for a polyaxial screw as set forth in claim 8, further including a threaded set screw configured to engage threads formed on the first end of said connector assembly, said set screw operatively engaging said rod which in turn directly presses against said saddle which in turn bears against the spherical connector causing a lower portion of said spherical connector to bear against an inner spherical surface formed on the internal passageway of the second end of the connector assembly.

10. The assembly for a polyaxial screw as set forth in claim 9, wherein said rod further contacts said first side wall and second side wall.

11. The assembly for a polyaxial screw as set forth in claim 9, wherein each of the first and second side walls includes a recess to provide a gripping surface that can cooperate with a tool whereby a torque can be applied to the connector assembly during tightening or removal of said set screw.

12. The assembly for a polyaxial screw as set forth in claim 9, wherein each of the first and second side walls includes a recess to provide a mounting surface for an extender tube to facilitate minimally invasive spinal procedures.

* * * * *